United States Patent
Hirose et al.

(10) Patent No.: US 8,770,752 B2
(45) Date of Patent: Jul. 8, 2014

(54) OPHTHALMIC APPARATUS, OPHTHALMIC SYSTEM, PROCESSING APPARATUS, AND BLOOD FLOW VELOCITY CALCULATION METHOD

(75) Inventors: Futoshi Hirose, Yokohama (JP); Hiroshi Imamura, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 116 days.

(21) Appl. No.: 13/305,629

(22) Filed: Nov. 28, 2011

(65) Prior Publication Data

US 2012/0140170 A1    Jun. 7, 2012

(30) Foreign Application Priority Data

Dec. 2, 2010 (JP) .................................. 2010-269741

(51) Int. Cl.
- A61B 3/10 (2006.01)
- A61B 3/14 (2006.01)
- A61B 5/02 (2006.01)
- A61B 3/12 (2006.01)

(52) U.S. Cl.
CPC ............. A61B 3/1233 (2013.01); A61B 3/1241 (2013.01); A61B 3/12 (2013.01); A61B 3/14 (2013.01)
USPC ............................. 351/206; 351/221; 600/504

(58) Field of Classification Search
USPC ................... 351/205, 206, 221; 600/504, 505
See application file for complete search history.

(56) References Cited

U.S. PATENT DOCUMENTS 5,549,114 A * 8/1996 Petersen et al. ............... 600/504
5,976,502 A   11/1999 Khoobehi 2007/0291230 A1 * 12/2007 Yamaguchi et al. .......... 351/221
2008/0045848 A1   2/2008 Lacombe
2013/0070201 A1 * 3/2013 Shahidi et al. ............... 351/206

FOREIGN PATENT DOCUMENTS

JP    2003-180641 A    7/2003
JP    2007-530197 A   11/2007

OTHER PUBLICATIONS

Martin et al.,Direct and Noninvasive Assessment of Parafoveal Capillary Leukocyte Velocity, American Academy of Ophthalmology, Dec. 2005, vol. 112, No. 12, pp. 2219-2224.
Hossain et al., "In Vivo Cell Tracking by Scanning Laser Ophthalmoscopy: Quantification of Leukocyte Kinetics", Investigative Ophthalmology & Visual Science, January 11998, Vo. 39, No. 10, pp. 1879-1887, Chapter "SLO and Image Analysis".
Sakata et al., "Relationship between Macular Microcirculation and Progression of Diabetic Macular Edema",; Ophthalmology, J.B. Lippincott Co., Philadelphia, PA, US, vol. 113, No. 8, Aug. 1, 2006, pp. 1385-1391.
Nishiwaki et al., "Quantitative Evaluation of Leukocyte Dynamics in Retinal Microcirculation", Investigative Ophthalmology & Visual Science, Jan. 1, 1995, vol. 36, No. 1, pp. 123-130, Chapter "Materials and Methods".

* cited by examiner

*Primary Examiner* — Mahidere Sahle
(74) *Attorney, Agent, or Firm* — Canon U.S.A., Inc., IP Division

(57) ABSTRACT

An ophthalmic apparatus includes an irradiation unit configured to irradiate a subject's eye with a measurement beam scanned by a scanning unit, an acquisition unit configured to acquire an image of the subject's eye based on a return beam returned from the subject's eye, of the measurement beam irradiated by the irradiation unit, and a calculation unit configured to calculate a blood flow velocity of the subject's eye based on a displacement between a position of a blood cell in a first image obtained by the acquisition unit and a position of the blood cell in a second image obtained by the acquisition unit at a different time from the first image and on a difference between time when an image of the blood cell in the first image is obtained and time when an image of the blood cell in the second image is obtained.

11 Claims, 5 Drawing Sheets

OPHTHALMIC APPARATUS, OPHTHALMIC SYSTEM, PROCESSING APPARATUS, AND BLOOD FLOW VELOCITY CALCULATION METHOD

BACKGROUND OF THE INVENTION

1. Field of the Invention

The present invention relates a blood flow velocity calculation apparatus and a method thereof, and more particularly, to an ophthalmic apparatus, an ophthalmic system, a processing apparatus, and a blood flow velocity calculation method used for an ophthalmic care.

2. Description of the Related Art

A scanning laser ophthalmoscope (SLO) which is an ophthalmic apparatus using the principle of a confocal laser microscope is a device that performs raster scan on an eye fundus with a laser as a measurement beam to obtain high resolution planar images at high speed from an intensity of return beam of the measurement beam.

Hereinafter, the device that captures such a planar image will be referred to as an SLO apparatus.

In recent years, the SLO apparatus has been able to acquire a planar image of a retina with an improved horizontal resolution by increasing a beam diameter of a measurement beam. However, with the increase in the beam diameter of the measurement beam, the acquired planar image of the retina has an issue of a low signal-to-noise (SN) ratio and a low resolution due to an aberration of a subject's eye.

To solve this issue, developed is an adaptive optics SLO apparatus including an adaptive optics system which measures the aberration of the subject's eye in real time using a wavefront sensor and corrects the aberration of the measurement beam or the return beam thereof occurring in the subject's eye using a wavefront correction device. In this way, the planar image having a high horizontal resolution can be acquired.

Moreover, a technique for successively acquiring the planar images of the retina with a high horizontal resolution using an adaptive optics SLO apparatus and calculating the blood flow velocity from a moving distance of a blood cell in a capillary vessel is discussed in "Joy A. Martin, Austin Roorda, Direct and Noninvasive Assessment of Parafoveal Capillary Leukocyte Velocity. Ophthalmology, 2005, 112: 2219". This document discusses a technique for calculating the blood flow velocity by utilizing a period (a period required for acquiring one planar image) from when the first planar image is acquired to when the second planar image is acquired.

As described above, the SLO apparatus is a device that performs raster scan on the retina with a measurement beam using a scanning unit to obtain planar images of the retina. Thus, an image capturing timing varies from position to position in the acquired planar image.

Therefore, the period (a period required for acquiring one planar image) from when the first planar image is acquired to when the second planar image is acquired is different from a period from when the scanning unit acquires a position (first position) of a blood cell in the first planar image to when the scanning unit acquires a position (second position) of the blood cell in the second planar image. Accordingly, the technique discussed in the above document cannot accurately calculate the blood flow velocity.

SUMMARY OF THE INVENTION

According to an aspect of the present invention, an ophthalmic apparatus includes an irradiation unit configured to irradiate a subject's eye with a measurement beam scanned by a scanning unit, an acquisition unit configured to acquire an image of the subject's eye based on a return beam returned from the subject's eye, of the measurement beam irradiated by the irradiation unit, and a calculation unit configured to calculate a blood flow velocity of the subject's eye based on a displacement between a position of a blood cell in a first image obtained by the acquisition unit and a position of the blood cell in a second image obtained by the acquisition unit at a different time from the first image and on a difference between time when an image of the blood cell in the first image is obtained and time when an image of the blood cell in the second image is obtained.

According to another aspect of the present invention, an ophthalmic system includes an irradiation unit configured to irradiate a subject's eye with a measurement beam scanned by a scanning unit, an acquisition unit configured to acquire an image of the subject's eye based on a return beam returned from the subject's eye, of the measurement beam irradiated by the irradiation unit, and a calculation unit configured to calculate a blood flow velocity of the subject's eye based on a displacement between a position of a blood cell in a first image obtained by the acquisition unit and a position of the blood cell in a second image obtained by the acquisition unit at a different time from the first image and on a difference between time when an image of the blood cell in the first image is obtained and time when an image of the blood cell in the second image is obtained.

According to yet another aspect of the present invention, an information processing apparatus includes a displacement calculation unit configured to calculate a displacement between a position of a blood cell in a first image obtained by an acquisition unit configured to acquire an image of a subject's eye and a position of the blood cell in a second image obtained by the acquisition unit at a different time from the first image based on a return beam, from the subject's eye, of a measurement beam irradiated by an irradiation unit configured to irradiate the subject's eye with the measurement beam scanned by a scanning unit, a time calculation unit configured to calculate a difference between time when an image of the blood cell in the first image is obtained and time when an image of the blood cell in the second image is obtained, and a calculation unit configured to calculate a blood flow velocity of the subject's eye based on the displacement calculated by the displacement calculation unit and the difference calculated by the time calculation unit.

According to yet another aspect of the present invention, a method for calculating a blood flow velocity includes irradiating a subject's eye with a measurement beam scanned by a scanning unit, acquiring an image of the subject's eye based on a return beam, from the subject's eye, of the irradiated measurement beam, and calculating a blood flow velocity of the subject's eye based on a displacement between a position of a blood cell in an acquired first image and a position of the blood cell in a second image acquired at a different time from the first image and a difference between time when an image of the blood cell in the first image is obtained and time when an image of the blood cell in the second image is obtained.

According to the above aspects of the present invention, it is possible to utilize the scanning period (the scanning speed and the scanning interval of the scanning unit) required for the scanning unit to scan the distance from the position corresponding to the first position in the second image to the second position as well as the time required for acquiring one planar image. In this way, since the period from when the scanning unit acquires the position (the first position) of the blood cell in the first planar image to when the scanning unit acquires the position (the second position) of the blood cell in the second planar image can be utilized, it is possible to accurately calculate the blood flow velocity.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

A blood flow velocity calculation apparatus (an ophthalmic apparatus or an ophthalmic system) according to the present invention includes an irradiation unit (also referred to as an illumination optical system) that irradiates a subject's eye with a measurement beam scanned by a scanning unit (for example, an XY scanner 119). Further, the blood flow velocity calculation apparatus includes an acquisition unit (for example, a personal computer (PC) 125) that acquires an image (for example, a planar image) of the subject's eye based on a return beam, from the subject's eye, of the measurement beam irradiated by the irradiation unit.

Moreover, the blood flow velocity calculation apparatus includes a calculation unit (for example, the PC 125) that calculates the blood flow velocity of the subject's eye based on a displacement between a position of a blood cell in a first image obtained by the acquisition unit and a position of the blood cell in a second image obtained by the acquisition unit at a different time from the first image and a difference between the time when an image of the blood cell in the first image is obtained and the time when an image of the blood cell in the second image is obtained.

The calculation unit included in the blood flow velocity calculation apparatus may calculate the blood flow velocity of the subject's eye based on the displacement and a period required for the scanning unit to scan the measurement beam from the position of the blood cell in the first image to the position of the blood cell in the second image.

The blood flow velocity calculation apparatus may include a display unit (for example, a display of the PC 125) that displays the image of the subject's eye acquired by the acquisition unit. Further, the blood flow velocity calculation apparatus may include an image processing unit (for example, the PC 125) that performs image processing on the first and second images so that the blood cell included in the first and second images is highlighted and displayed on the display unit. Furthermore, the blood flow velocity calculation apparatus may include a selection unit (for example, a mouse of the PC 125) that selects the blood cell included in the first and second images displayed on the display unit.

The calculation unit included in the blood flow velocity calculation apparatus may calculate the blood flow velocity of the subject's eye based on the displacement and the difference of the blood cell included in the first and second images, selected by the selection unit. The blood flow velocity calculation apparatus may include an image creation unit (for example, the PC 125) that creates a spatiotemporal image using the first and second images.

Further, the blood flow velocity calculation apparatus may include an aberration measurement unit (for example, a wavefront sensor 155) that measures aberration occurring in the subject's eye, and a spatial light modulation unit (for example, spatial light modulators 159-1 and 159-2) that is disposed at a position conjugate to the aberration measurement unit and modulates at least one of the measurement beam and the return beam. Furthermore, the blood flow velocity calculation apparatus may include a control unit (for example, a spatial light modulator driver 184) that controls an amount of modulation in the spatial light modulation unit based on the measurement result by the aberration measurement unit to correct the aberration.

Moreover, the blood flow velocity calculation apparatus may include a splitting unit (for example, an optical coupler 131) that splits a beam from a light source into the measurement beam and a reference beam, and an interference unit (for example, the optical coupler 131) that causes the return beam resulting from the measurement beam irradiated to the subject's eye to interfere with the reference beam having passed through a reference optical path. Furthermore, the blood flow velocity calculation apparatus may include a detection unit (for example, a line sensor 139) that detects the intensity of an interference signal resulting from the interference, and a tomographic image acquisition unit (for example, the PC 125) that acquires a tomographic image of the subject's eye based on the intensity detected by the detection unit.

Moreover, the blood flow velocity calculation apparatus may include a conversion unit (for example, a detector 138) that detects the return beam, from the subject's eye, of the measurement beam and converts the detected beam into an electrical signal, and a light guiding unit (for example, a movable beam splitter 161) that guides the return beam to the conversion unit on an optical path that connects the light source and the subject's eye.

Furthermore, the acquisition unit included in the blood flow velocity calculation apparatus may acquire an image of the subject's eye based on the intensity of the electrical signal obtained by the conversion unit.

An information processing apparatus according to the present invention includes a displacement calculation unit (for example, the PC 125) that calculates a displacement between a position of a blood cell in a first image which is obtained by an acquisition unit that acquires an image of a subject's eye and a position of the blood cell in a second image obtained by the acquisition unit at a different time from the first image based on a return beam from the subject's eye, of a measurement beam irradiated by an irradiation unit that irradiates the subject's eye with the measurement beam scanned by a scanning unit. Further, the information processing apparatus includes a time calculation unit (for example, the PC 125) that calculates a difference between time when an image of the blood cell in the first image is obtained and time when an image of the blood cell in the second image is obtained.

Moreover, the information processing apparatus includes a calculation unit (for example, the PC 125) that calculates a blood flow velocity of the subject's eye based on the displacement calculated by the displacement calculation unit and the difference calculated by the time calculation unit.

A method for calculating a blood flow velocity according to the present invention includes an irradiation operation for irradiating a subject's eye with a measurement beam scanned by a scanning unit, and an acquisition operation for acquiring an image of the subject's eye based on a return beam from the subject's eye, of the measurement beam irradiated in the irradiation operation. Further, the method includes a calculation operation for calculating a blood flow velocity of the subject's eye based on a displacement between a position of a blood cell in a first image acquired in the acquisition operation and a position of the blood cell in a second image acquired in the acquisition operation at a different time from the first image and a difference between time when an image of the blood cell in the first image is obtained and time when an image of the blood cell in the second image is obtained.

With this configuration, it is possible to utilize a scanning period (a scanning speed and an interval of the scanning unit) required for the scanning unit to scan a distance from a position corresponding to a first position in the second image to a second position as well as the time required for acquiring one planar image. In this way, since the period from when the scanning unit acquires the position (the first position) of the blood cell in the first planar image to when the scanning unit acquires the position (the second position) of the blood cell in the second planar image can be utilized, it is possible to accurately calculate the blood flow velocity.

In a first exemplary embodiment, an SLO apparatus according to the present invention will be described as an example of an optical image capturing apparatus. In particular, an SLO apparatus which includes an adaptive optics system and which captures a high horizontal resolution planar image (SLO image) of a retina and calculates a blood flow velocity using the acquired planar image will be described.

In the present exemplary embodiment, the SLO apparatus is configured to correct an optical aberration of a subject's eye using a spatial light modulator to acquire a planar image, so that a satisfactory planar image can be obtained regardless of a diopter of the subject's eye and the optical aberration.

Although the SLO apparatus includes a adaptive optics system to capture a high horizontal resolution planar image, the SLO apparatus may not include the adaptive optics system as long as it can capture the image of a blood vessel or a blood cell.

<Overall Configuration>

Figure 1:
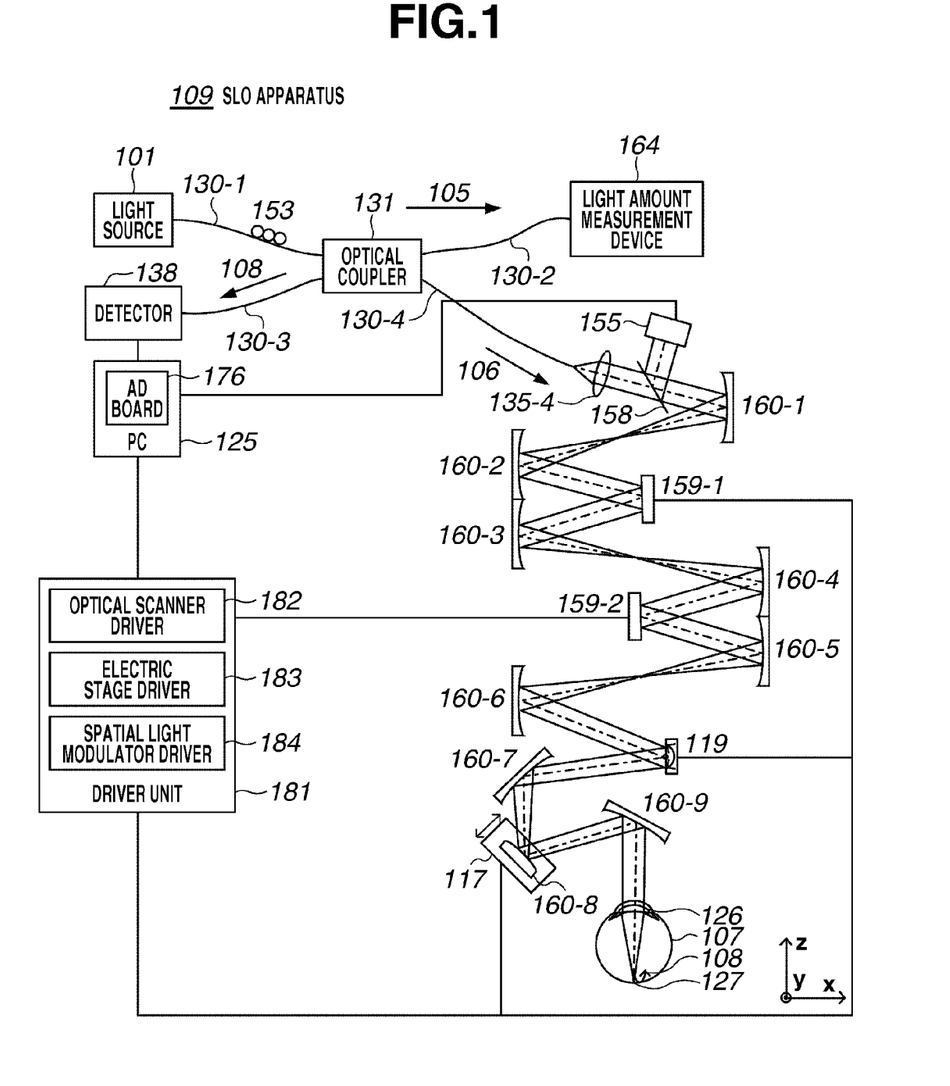
FIG. 1 illustrates an overall configuration of an SLO apparatus according to a first exemplary embodiment of the present invention.

First, a schematic configuration of an SLO apparatus 109 according to the present exemplary embodiment will be described in detail with reference to FIG. 1. Light emitted from a light source 101 is split into a reference beam 105 and a measurement beam 106 by an optical coupler 131. The measurement beam 106 is guided to a subject's eye 107 which is an observation target after passing through a single-mode fiber 130-4, spatial light modulators 159-1 and 159-2, an XY scanner 119, spherical mirrors 160-1 to 160-9, and the like.

The measurement beam 106 becomes a return beam 108 by being reflected or scattered by the subject's eye 107 and enters a detector 138. The detector 138 converts a light intensity of the return beam 108 into a voltage signal, and a planar image of the subject's eye 107 is formed using the voltage signal. The blood flow velocity is calculated using the acquired planar image.

In the present exemplary embodiment, although the overall optical system is configured using a reflection optical system which mainly uses spherical mirrors, the overall optical system may be configured by a refractive optical system which uses lenses instead of spherical mirrors.

In the present exemplary embodiment, although a reflection type spatial light modulator is used, a transmission type spatial light modulator may be used.

<Light Source>

Next, the periphery of the light source 101 will be described. The light source 101 is a super luminescent diode (SLD) which is a typical low coherent light source. The light source 101 has a wavelength of 830 nm and a bandwidth of 50 nm. In the present exemplary embodiment, a low coherent light source is used to acquire a planar image with small speckle noise. Although the SLD is used as the light source, an amplified spontaneous emission (ASE) or the like may be used as long as it can emit low coherent light.

Considering eyes are to be measured, near-infrared light is suitable for the wavelength of the light source. In addition, since the wavelength affects the horizontal resolution of an obtained planar image, the wavelength which is as short as possible can be adopted, and in the present exemplary embodiment, is 830 nm. Other wavelengths may be adopted according to a measurement region of an observation target.

The beam emitted from the light source 101 is split into the reference beam 105 and the measurement beam 106 in the proportion of 96:4 after passing through the single-mode fiber 130-1 and the optical coupler 131. A polarization controller 153 is disposed between the light source 101 and the optical coupler 131.

<Reference Optical Path>

Next, the optical path of the reference beam 105 will be described. The reference beam 105 split by the optical coupler 131 enters a light amount measurement device 164 through an optical fiber 130-2. The light amount measurement device 164 is used for the purpose of measuring the light amount of the reference beam 105 and monitoring the light amount of the measurement beam 106.

<Measurement Optical Path>

Next, the optical path of the measurement beam 106 will be described. The measurement beam 106 split by the optical coupler 131 is guided to a lens 135-4 via the single-mode fiber 130-4 and is adjusted to be a parallel light having a beam diameter of 4 mm.

The measurement beam 106 passes through a beam splitter 158 and enters a first spatial light modulator 159-1 after being reflected by the spherical mirrors 160-1 and 160-2. The first spatial light modulator 159-1 is disposed in a direction of modulating the phase of a P-polarized light (parallel to the sheet surface).

Next, the measurement beam 106 enters a second spatial light modulator 159-2 after being modulated by the first spatial light modulator 159-1 and reflected by spherical mirrors 160-3 and 160-4. The second spatial light modulator 159-2 is disposed in a direction of modulating the phase of an S-polarized light (perpendicular to the sheet surface). Since the spatial light modulators 159-1 and 159-2 generally perform modulation using the orientation of liquid crystals, the spatial light modulators 159-1 and 159-2 modulate only the polarization component of a specific direction.

Thus, as described above, by successively modulating the P-polarization component and the S-polarization component of the measurement beam 106, it is possible to modulate all polarization components of the measurement beam 106.

As described above, although it is desirable to dispose the spatial light modulators 159-1 and 159-2 so that the orientation directions of the liquid crystals thereof are perpendicular to each other, the orientation directions are not limited to being perpendicular but may be different from each other.

The spatial light modulators 159-1 and 159-2 are controlled by the spatial light modulator driver 184 in a driver unit 181 from the PC 125.

Subsequently, the measurement beam 106 enters a mirror of the XY scanner 119 after being modulated by the second spatial light modulator 159-2 and reflected by the spherical mirrors 160-5 and 160-6. Although the XY scanner 119 is described as including one mirror for the sake of simplicity, actually, the XY scanner 119 is one in which two mirrors of the X scanner and the Y scanner are disposed next to each other, and which performs raster scan over the retina 127 in a direction perpendicular to an optical axis. The center of the measurement beam 106 is adjusted to be identical to the rotation center of the mirror of the XY scanner 119.

The X scanner is a scanner that scans the measurement beam 106 in a direction parallel to the sheet surface, and in the present exemplary embodiment, a resonance scanner is used. A driving frequency of the X scanner is about 7.9 kHz. The Y scanner is a scanner that scans the measurement beam 106 in a direction perpendicular to the sheet surface, and in the present exemplary embodiment, a galvano scanner is used. The Y scanner uses signal having a driving waveform of sawtooth wave, a driving frequency of 64 Hz, and a duty ratio of 16%. The driving frequency of the Y scanner is an important parameter in calculating the blood flow velocity since it determines an image capturing frame rate of the SLO apparatus 109. A different driving frequency may be used according to the blood flow velocity to be measured.

The XY scanner 119 is controlled by an optical scanner driver 182 in the driver unit 181 from the PC 125. The spherical mirrors 160-7 to 160-9 are optical systems for scanning the retina 127 and perform the role of scanning the retina 127 about the vicinity of the cornea 126 with the measurement beam 106.

Although the measurement beam 106 has a beam diameter of 4 mm, the beam diameter may be increased to acquire a high resolution tomographic image.

A motor-driven stage 117 is configured to move in a direction indicated by an arrow in the drawing and to adjust the position of a spherical mirror 160-8 attached thereto. The motor-driven stage 117 is controlled by a motor-driven stage driver 183 in the driver unit 181 from the PC 125.

By adjusting the position of the spherical mirror 160-8, it is possible to focus the measurement beam 106 on a predetermined layer of the retina 127 of the subject's eye 107 and observe the subject's eye 107.

The SLO apparatus 109 according to the present exemplary embodiment can cope with the subject's eye 107 having refractive error. When the measurement beam 106 enters the subject's eye 107, the measurement beam 106 becomes the return beam 108 due to reflection or scattering from the retina 127, and the return beam 108 reaches the detector 138 through the single-mode fiber 130-3 by being guided again by the optical coupler 131. As the detector 138, an avalanche photo diode (APD) or a photomultiplier tube (PMT) which is a high-speed, high-sensitive optical sensor can be used, for example.

The S-polarized light and the P-polarized light of the return beam 108 are modulated again by the second spatial light modulator 159-2 and the first spatial light modulator 159-1, respectively.

A part of the return beam 108 split by the beam splitter 158 enters the wavefront sensor 155, and the aberration of the return beam 108 occurring in the subject's eye 107 is measured.

In the present exemplary embodiment, although the SLO apparatus 109 uses one wavefront sensor 155, the aberration may be measured for each polarization using two wavefront sensors.

The wavefront sensor 155 is electrically connected to the PC 125. The spherical mirrors 160-1 to 160-9 are disposed so that they are optically conjugate to the cornea 126, the XY scanner 119, the wavefront sensor 155, and the spatial light modulators 159-1 and 159-2.

Thus, the wavefront sensor 155 can measure the aberration of the subject's eye 107. Moreover, the spatial light modulators 159-1 and 159-2 can correct the aberration of the subject's eye 107.

By controlling the spatial light modulators 159-1 and 159-2 in real time based on the aberration obtained from the measurement result by the wavefront sensor 155, the aberration occurring in the subject's eye 107 can be corrected. In this way, the planar image having a higher horizontal resolution can be acquired.

In the present exemplary embodiment, although the spherical mirror 160-8 is used, a cylindrical mirror may be used instead of the spherical mirror 160-8 according to the aberration (refractive error) of the subject's eye 107.

A new lens may be added to the optical path of the measurement beam 106. In the present exemplary embodiment, although the aberration is measured by the wavefront sensor 155 using the measurement beam 106, another light source may be used for measurement of the aberration. Further, another optical path may be formed for measurement of the aberration.

For example, an aberration measurement beam may be incident using a beam splitter from a space between the spherical mirror 160-9 and the cornea 126.

<Measurement System>

Next, the configuration of the measurement system will be described. The SLO apparatus 109 can acquire the planar image (SLO image) which is formed based on the intensity of the return beam 108 from the retina 127.

The return beam 108 which is the beam reflected or scattered by the retina 127 enters the detector 138 after passing the spherical mirrors 160-1 to 160-9, the spatial light modulators 159-1 and 159-2, and the optical coupler 131, and the intensity of the beam is converted into a voltage signal by the detector 138.

The voltage signal obtained by the detector 138 is converted into a digital value by an analog-to-digital (AD) board 176 in the PC 125, and the digital data is processed by the PC 125 in synchronization with the operation and the driving frequency of the XY scanner 119, so that the planar image is formed. An acquisition speed of the AD board 176 is 15 MHz. A part of the return beam 108 split by the beam splitter 158 enters the wavefront sensor 155, and the aberration of the return beam 108 is measured.

The wavefront sensor 155 is a Shack-Hartmann wavefront sensor. The obtained aberration is expressed by Zernike polynomial, which represents the aberration of the subject's eye 107.

The Zernike polynomial includes a tilt (inclination) term, a defocus term, an astigmatism term, a coma term, and a trefoil term.

<SLO Image Acquisition Method>

Next, a planar image (SLO image) acquisition method will be described with reference to FIGS. 2A to 2D. The SLO apparatus 109 can acquire the planar image of the retina 127 by controlling the XY scanner 119 and acquiring the intensity of the return beam 108 using the detector 138. In the present exemplary embodiment, a method for acquiring the planar image (a plane perpendicular to the optical axis) of the retina 127 will be described.

Figures 2A, 2B:
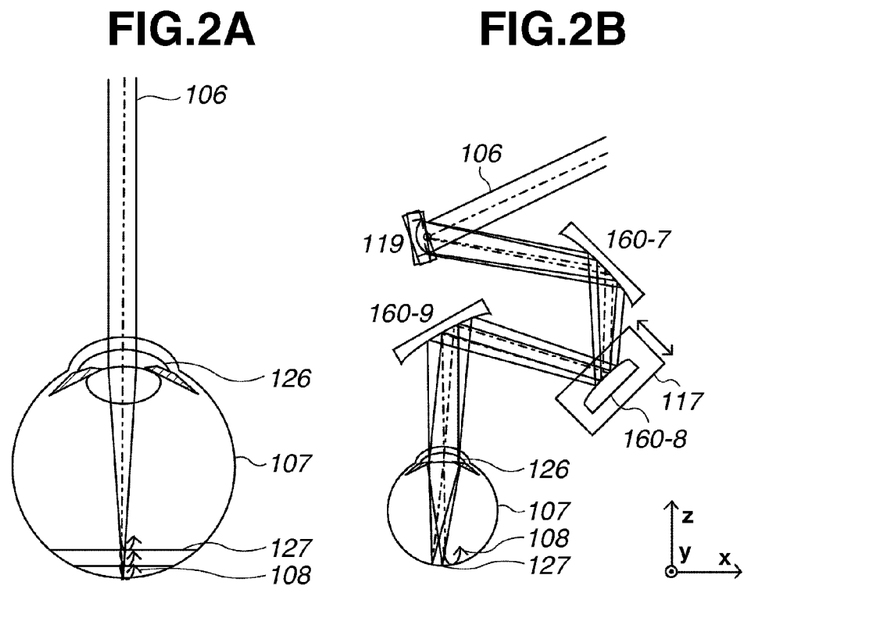
FIGS. 2A to 2D illustrate an image acquisition method in the SLO apparatus according to the first exemplary embodiment of the present invention.

FIG. 2A is a schematic view of the subject's eye 107 and illustrates a state where the subject's eye 107 is observed by the SLO apparatus 109. As illustrated in FIG. 2A, when the measurement beam 106 enters the retina 127 through the cornea 126, the measurement beam 106 becomes the return beam 108 due to reflection or scattering at various positions, and the return beam 108 reaches the detector 138.

Further, as illustrated in FIG. 2B, the XY scanner 109 is moved in the X direction, and the intensity of the return beam 108 is detected, so that information at each position on the X axis can be obtained.

Figure 2C:
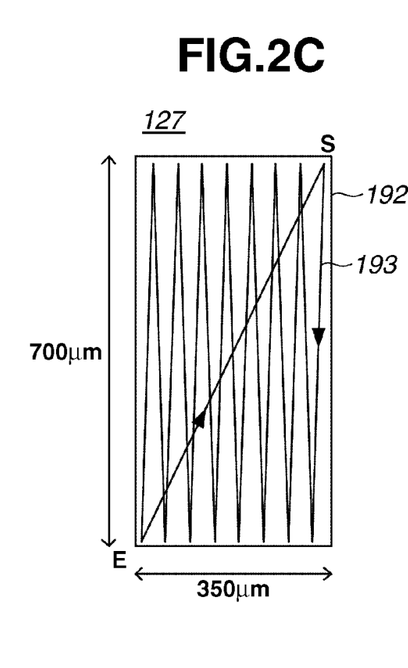

Further, as illustrated in FIG. 2C, the XY scanner 109 is moved in both the X and Y axes, and the measurement beam 106 is raster-scanned along a trajectory 193 on an image capturing range 192 where the retina 127 is present. In this state, the intensity of the return beam 108 is detected, so that a two-dimensional distribution of the intensity of the return beam 108 can be obtained, which is the planar image 177 (see FIG. 2D).

The measurement beam 106 is scanned from a right point S to a bottom left point E, and during the scanning, the intensity of the return beam 108 is used for forming the planar image 177. The trajectory 193 from the point E to the point S is the movement of the measurement beam 106 for preparation of the image capturing of the planar image 177. The period required for the scanning takes 84% for the point S to the point E and 16% for the point E to the point S for the trajectory 193 illustrated in the drawing, and this ratio is based on the duty ratio of the driving waveform of the Y scanner described above. In FIG. 2C, for the sake of simplicity, the number of times of the scanning in the X direction of the trajectory 193 is smaller than the actual number of times.

Figure 2D:
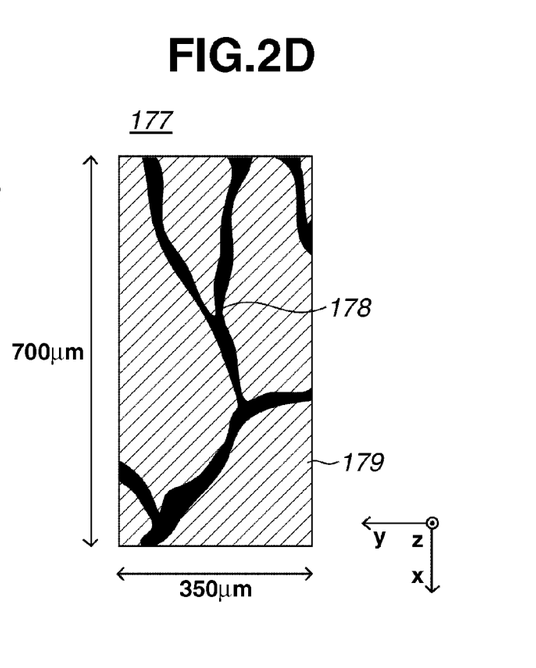

The planar image 177 has a size of 700×350 μm, and the time required for acquisition is about 15.6 millisecond. This time is based on the driving frequency of the Y scanner.

In the planar image 177, a visual cell group 179 where the intensity of the return beam 108 is relatively high is visualized brightly, whereas a blood vessel 178 where the intensity is relatively low is visualized darkly. Further, blood cells (not illustrated) are visualized brightly in the blood vessel 178. By acquiring the planar images 177 continuously over time, the movement of blood cells in the vessel 178 can be visualized.

Spatiotemporal images may be created by extracting the blood vessel 178 where blood cells are visualized from the planar images 177 continuously acquired and superimposing the extracted planar images 177 in the order of capturing. In this way, the movement of the blood cells and the blood flow velocity can be understood easily.

<Blood Velocity Calculation Method>

Next, a method for calculating the blood flow velocity from the acquired planar image will be described with reference to FIGS. 3A and 3B. The SLO apparatus 109 can successively acquire the planar images by successively raster-scanning the image capturing range where the retina 127 is present using the XY scanner 119.

Figure 3A:
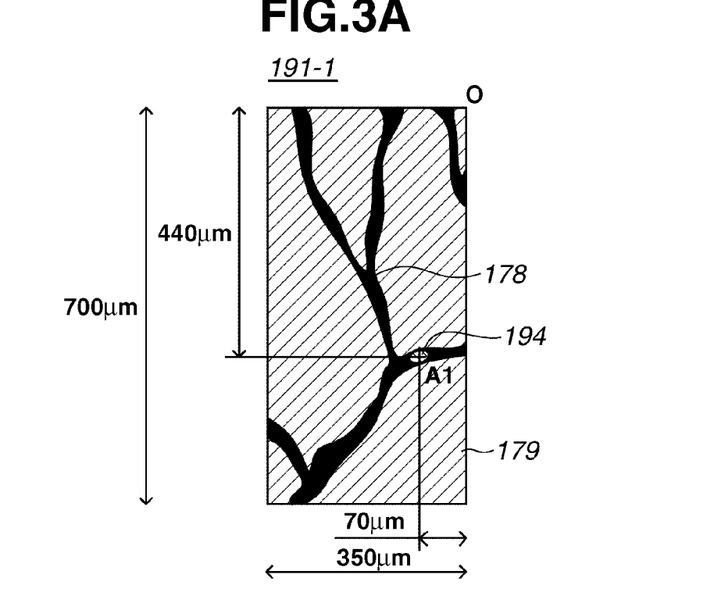
FIGS. 3A and 3B illustrate a blood flow velocity calculation method in the SLO apparatus according to the first exemplary embodiment of the present invention.
Figure 3B:
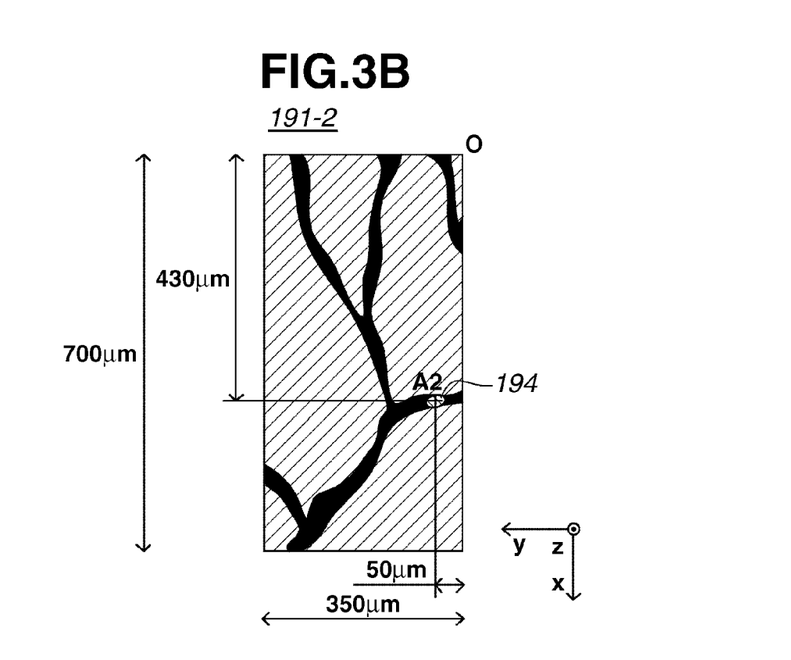

FIGS. 3A and 3B illustrate planar images 191-1 and 191-2 acquired continuously over time by the above-described method. The planar images 191-1 and 191-2 are displayed in parallel on the display of the PC 125. As illustrated in FIGS. 3A and 3B, the planar images 191-1 and 191-2 include the blood vessel 178, the visual cell group 179, and the blood cell 194. A method for calculating the moving velocity of the blood cell 194, namely the blood flow velocity will be described with reference to the planar images 191-1 and 191-2.

The blood flow velocity calculation method involves the following operations (1) to (5). The following operations may be automatically performed using a computer such as the PC 125.

(1) Image processing is performed on each of the planar images 191-1 and 191-2 so that the blood cell 194 is highlighted. For example, by regarding the visual cell group 179 to be immovable over time, a difference between the planar images 191-1 and 191-2 is calculated to thereby highlight the blood cell 194. Moreover, distortion due to involuntary eye movement during visual-fixation may be corrected with respect to the planar images 191-1 and 191-2.

(2) The position of the blood cell 194 in each of the planar images 191-1 and 191-2 is detected. If the top right corner of the image is the origin O (0, 0), the positions (in units of μm) of the blood cell 194 in the planar images 191-1 and 191-2 are A1 (70, 440) and A2 (50, 430), respectively. The position of the blood cell 194 may be detected automatically by a computer or the like, and may be detected by an examiner, who is an operator, selecting the blood cell 194 using a mouse of the PC 125.

(3) A moving distance of the blood cell 194 is calculated using the positions thereof detected in the operation (2). The moving distance L (in units of μm) is L (20, 10) which is the difference between the positions A1 and A2.

(4) A movement period T which is the time required for moving the moving distance L calculated in the operation (3) is calculated by taking the raster scanning direction into consideration. When the raster scanning direction is taken into consideration, since the size of the planar image 177 is 700× 350 μm (in the present exemplary embodiment, 400×200 pixels), and the frequency and the duty ratio of the Y scanner are 64 Hz and 16%, respectively, the movement period T becomes 0.0149 seconds $(=(1/64)\times(1-0.84\times20/350))$. Since the X scanner moves at a sufficiently higher speed than the Y scanner, the movement period in the X direction is not considered.

(5) Since a moving velocity V (in units of mm/s) of the blood cell 194 is expressed as V=L/T, V=(1.342, 0.671), and the blood flow velocity is 1.50 mm/s.

As described above, by visualizing a movement of a blood cell in a blood vessel from planar images which are continuously captured, calculating the difference in time when the blood cell is captured from the position of the blood cell, and calculating the moving velocity of the blood cell based on the time difference, it is possible to calculate a more accurate blood flow velocity.

By performing appropriate image processing on the captured planar images and highlighting the blood cell, it is possible to calculate a more accurate blood flow velocity. Further, the possibility of calculating the blood flow velocity can be increased.

By manually selecting the blood cell from the planar image, it is possible to increase the possibility of calculating the blood flow velocity in a planar image with a low SN ratio, for example.

Further, by automatically selecting the blood cell from the planar image, it is possible to calculate the blood flow velocity more easily.

Further, by creating and displaying the spatiotemporal image using the planar images captured continuously, it is possible to easily grasp the movement of the blood cell and the blood flow velocity.

The blood flow velocity calculation apparatus according to the present exemplary embodiment includes the spatial light modulation unit capable of modulating at least one of the measurement beam and the return beam, the aberration measurement unit that measures the aberration occurring in the subject's eye, and the control unit that controls the amount of modulation in the spatial light modulation unit based on the measurement result by the aberration measurement unit to correct the aberration. Further, the spatial light modulation unit is configured to perform modulation at a position that is optically conjugate to the aberration measurement unit. With this configuration, the blood flow velocity calculation apparatus can acquire a planar image with a high horizontal resolution and calculate a blood flow velocity of a finer blood vessel.

Further, the blood flow velocity calculation apparatus according to the present exemplary embodiment calculates the moving velocity of the blood cell based on the difference in time when the blood cell is captured. Thus, the difference between the blood flow velocity obtained with the present invention and the blood flow velocity obtained with the conventional technique is noticeable when the blood cell rarely moves in the Y direction of the planar image, for example. This is because in the conventional technique, the moving distance of the blood cell during the period when one planar image is acquired is subtracted even when the blood cell rarely moves. In other words, the present invention provides a noticeable effect over the conventional technique when the blood cell rarely moves in the Y direction of the planar image, for example.

In a second exemplary embodiment, a composite apparatus of an SLO apparatus and an optical coherence tomography (OCT) apparatus according to the present invention will be described as an example of an optical image capturing apparatus. In particular, a composite apparatus which includes an adaptive optics system and which captures both a high horizontal resolution planar image (SLO image) and a tomographic image (OCT image) of a retina and calculates a blood flow velocity using the acquired planar and tomographic images will be described.

In the present exemplary embodiment, the SLO apparatus is configured to correct an optical aberration of a subject's eye using a spatial light modulator to acquire a planar image, and a Fourier domain OCT apparatus is configured to acquire a tomographic image, so that favorable planar image and tomographic image are obtained regardless of a diopter of the subject's eye and an optical aberration.

<Overall Configuration>

Figure 4:
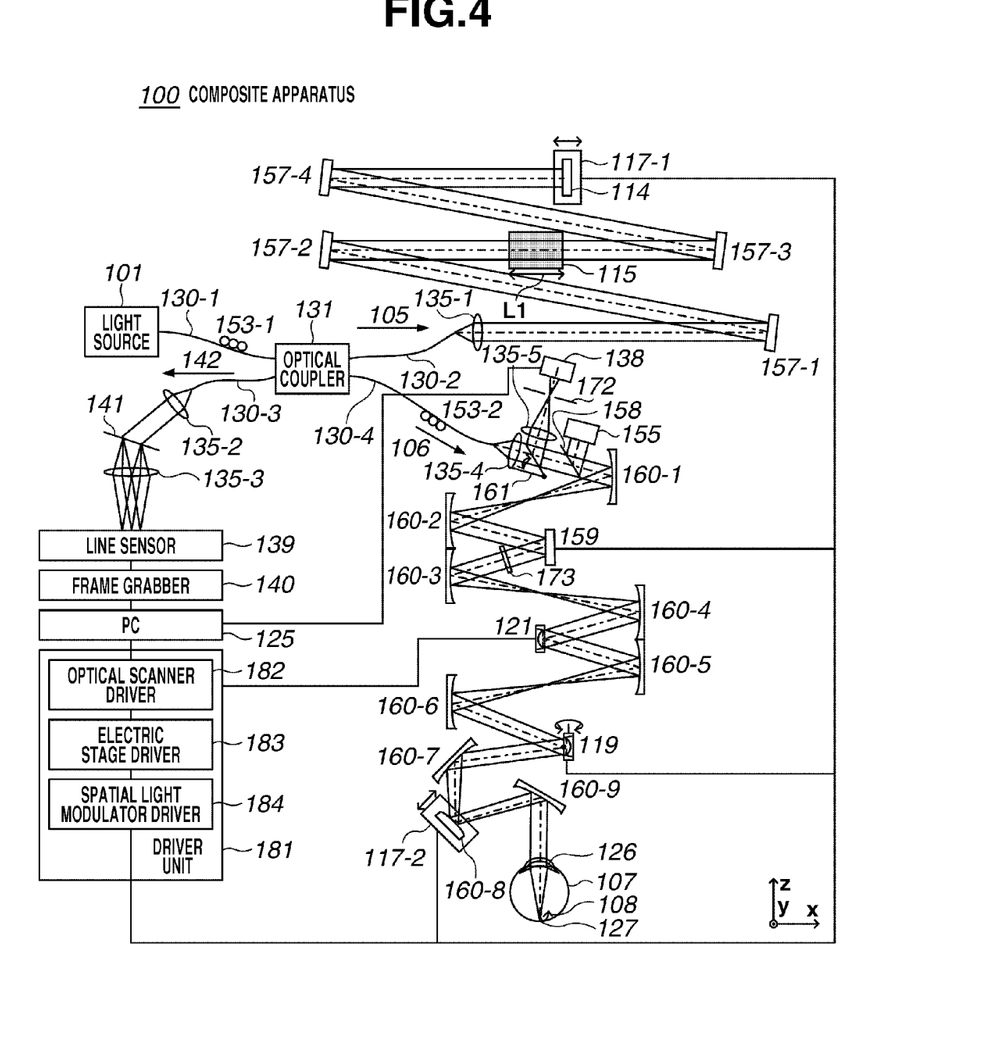
FIG. 4 illustrates an overall configuration of a composite apparatus according to a second exemplary embodiment of the present invention.

First, a schematic configuration of a composite apparatus 100 according to the present exemplary embodiment will be described in detail with reference to FIG. 4. In FIG. 4, the same constituent elements as the first exemplary embodiment illustrated in FIG. 1 are denoted by the same reference numerals, and the description thereof will not be repeated.

A beam emitted from a light source 101 is split into a reference beam 105 and a measurement beam 106 by an optical coupler 131. The measurement beam 106 is guided to a subject's eye 107 which is an observation target after passing through a single-mode fiber 130-4, a spatial light modulator 159, an XY scanner 119, an X scanner 121, spherical mirrors 160-1 to 160-9, and the like.

The measurement beam 106 becomes a return beam 108 by being reflected or scattered by the subject's eye 107 and enters a detector 138 or a line sensor 139. The detector 138 converts light intensity of the return beam 108 into a voltage signal, and a planar image of the subject's eye 107 is formed using the voltage signal. The blood flow velocity is calculated using the acquired planar image.

The line sensor 139 receives the reference beam 105 and the return beam 108, and tomographic images of the subject's eye 107 are formed. A three-dimensional movement of a blood vessel is visualized using a plurality of acquired tomographic images.

In the present exemplary embodiment, although the spatial light modulator is used as a device for correcting a wavefront aberration, a variable shape mirror may be used as long as it can correct the wavefront aberration.

<Light Source>

The light source 101 is the same as the first exemplary embodiment, and the description thereof will not be repeated. An SLD which is a low coherent light source is also suitable for capturing tomographic images.

<Reference Optical Path>

Next, the optical path of the reference beam 105 will be described. The reference beam 105 split by the optical coupler 131 is guided to a lens 135-1 after passing through the single-mode fiber 130-2 and is adjusted to be a parallel light having a beam diameter of 4 mm.

Subsequently, the reference beam 105 is guided to a mirror 114 which is a reference mirror by mirrors 157-1 to 157-4. Since an optical path length of the reference beam 105 is adjusted to be approximately the same as an optical path length of the measurement beam 106, it is possible to cause the reference beam 105 to interfere with the measurement beam 106.

Subsequently, the reference beam 105 is reflected by the mirror 114 and is again guided to the optical coupler 131. In this case, the reference beam 105 passes through a dispersion compensation glass 115 which compensates the reference beam 105 for dispersion of when the measurement beam 106 makes a round trip to the subject's eye 107.

In the present exemplary embodiment, a typical value of the average diameter of the eye of the Japanese is set to L1=23 mm. A motor-driven stage 117-1 is configured to move in a direction indicated by an arrow in the drawing and to adjust and control the optical path length of the reference beam 105. The motor-driven stage 117-1 is controlled by a motor-driven stage driver 183 in a driver unit 181 from a PC 125.

<Measurement Optical Path>

Next, the optical path of the measurement beam 106 will be described. The measurement beam 106 split by the optical coupler 131 is guided to a lens 135-4 via the single-mode fiber 130-4 and is adjusted to be a parallel light having a beam diameter of 4 mm. A polarization controller 153-1 or 153-2 is configured to adjust the polarization state of the measurement beam 106. In the present exemplary embodiment, the polarization state of the measurement beam 106 is adjusted to be a linearly polarized light parallel to the sheet surface.

The measurement beam 106 passes through a beam splitter 158 and a movable beam splitter 161 (also referred to as a branch unit) and enters a spatial light modulator 159 via spherical mirrors 160-1 and 160-2, and the measurement beam 106 is modulated by the spatial light modulator 159. The spatial light modulator 159 is a modulator that performs modulation utilizing the orientation of liquid crystal. The spatial light modulator 159 is disposed in a direction of modulating the phase of a linearly polarized light (P-polarized light) that is parallel to the sheet surface, and is identical to the direction of the polarization of the measurement beam 106.

The measurement beam 106 further passes through a polarizing plate 173 and enters a mirror of the X scanner 121 via spherical mirrors 160-3 and 160-4. The polarizing plate 173 has a function of guiding only the linearly polarized light parallel to the sheet surface among the return beam 108 to the spatial light modulator 159. The X scanner 121 is an X scanner that scans the measurement beam 106 in a direction parallel to the sheet surface, and in the present exemplary embodiment, a resonance scanner is used. A driving frequency of the X scanner 121 is about 7.9 kHz.

The measurement beam 106 enters a mirror of the XY scanner 119 via spherical mirrors 160-5 and 160-6. Although the XY scanner 119 is described as including one mirror for the sake of simplicity, actually, the XY scanner 119 is one in which two mirrors of the X and Y scanners are disposed next to each other. The center of the measurement beam 106 is adjusted to be identical to the rotation center of the mirror of the XY scanner 119. A driving frequency of the XY scanner 119 is variable in the range of ±500 Hz.

Spherical mirrors 160-7 to 160-9 are optical systems for scanning the retina 127 and perform the role of scanning the retina 127 about the vicinity of the cornea 126 with the measurement beam 106.

Although the measurement beam 106 has a beam diameter of 4 mm, the beam diameter may be increased to acquire a high resolution tomographic image. A motor-driven stage 117-2 is configured to move in a direction indicated by an arrow in the drawing and to adjust and control the position of the spherical mirror 160-8 attached thereto. Similarly to the motor-driven stage 117-1, the motor-driven stage 117-2 is controlled by the motor-driven stage driver 183.

By adjusting the position of the spherical mirror 160-8, it is possible to focus the measurement beam 106 on a predetermined layer of the retina 127 of the subject's eye 107 and observe the subject's eye 107. In the initial state, the position of the spherical mirror 160-8 is adjusted so that the measurement beam 106 can enter the cornea 126 as a parallel light.

The composite apparatus 100 according to the present exemplary embodiment can cope with the subject's eye 107 having refractive error. When the measurement beam 106 enters the subject's eye 107, the measurement beam 106 becomes the return beam 108 due to reflection or scattering from the retina 127, and the return beam 108 reaches a line camera 139 by being guided again by the optical coupler 131.

A part of the return beam 108 is reflected by the movable beam splitter 161 and guided to the detector 138 through the lens 135-5. A light blocking plate 172 having a pinhole has a function of blocking unnecessary beam that is not focused on the retina 127 among the return beam 108. Further, the light blocking plate 172 is disposed to be conjugate to the focusing position of the lens 135-5. The diameter of the pinhole of the light blocking plate 172 is 50 μm, for example. As the detector 138, an avalanche photo diode (APD) which is a high-speed, high-sensitive optical sensor is used, for example.

A part of the return beam 108 split by the beam splitter 158 enters a wavefront sensor 155. The wavefront sensor 155 is a Shack-Hartmann wavefront sensor.

The spherical mirrors 160-1 to 160-9 are disposed so that they are optically conjugate to the XY scanner 119, the X scanner 121, the cornea 126, the wavefront sensor 155, and the spatial light modulator 159. Thus, the wavefront sensor 155 can measure the aberration of the subject's eye 107. Further, the spatial light modulator 159 can correct the aberration of the subject's eye 107. Furthermore, by controlling the spatial light modulator 159 in real time based on the obtained aberration, it is possible to correct the aberration occurring in the subject's eye 107 and to acquire higher horizontal resolution tomographic images.

<Configuration of Measurement System>

Next, the configuration of the measurement system will be described. The composite apparatus 100 can acquire tomographic images (OCT images) and planar images (SLO images).

First, the measurement system for tomographic images will be described. The return beam 108 is multiplexed by the optical coupler 131. The multiplexed beam 142 is guided to a transmission type grating 141 through the single-mode fiber 130-3 and the lens 135-2 and is then dispersed for each wavelength, and enters the line camera 139 through the lens 135-3.

The line camera 139 converts the light intensity for each position (wavelength) into a voltage signal. The voltage signal is converted into a digital value by a frame grabber 140, so that tomographic images of the subject's eye 107 are formed in the PC 125.

The line camera 139 includes 1024 pixels, and can obtain the intensity of the multiplexed beam 142 for each wavelength (with a division of 1024).

Next, the measurement system for planar images will be described. A part of the return beam 108 is reflected by the movable beam splitter 161. The reflected beam reaches the detector 138 after the unnecessary beam is blocked by the light blocking plate 172, and the light intensity is converted into an electrical signal.

Data of the obtained electrical signal is processed by the PC 125 in synchronization with the scanning signal of the X scanner 121 and the XY scanner 119, so that planar images are formed.

A part of the return beam 108 split by the beam splitter 158 enters the wavefront sensor 155, and the aberration of the return beam 108 is measured. An image signal obtained by the wavefront sensor 155 is supplied to the PC 125, and an aberration is calculated. The obtained aberration is expressed by Zernike polynomial, which represents the aberration of the subject's eye 107.

The Zernike polynomial includes a tilt (inclination) term, a defocus term, an astigmatism term, a coma term, and a trefoil term.

<OCT Image Acquisition Method>

Next, a method for acquiring tomographic images (OCT images) using the composite apparatus 100 will be described with reference to FIGS. 5A to 5C. The composite apparatus 100 can acquire a tomographic image of the retina 127 by controlling the XY scanner 119 and acquiring an interference pattern with the line camera 139 using the X scanner 121 as a fixed mirror. The movable beam splitter 161 is controlled so that the return beam 108 is not guided to the detector 138. The X scanner 121 and the XY scanner 119 are controlled by the optical scanner driver 182 in the driver unit 181 from the PC 125 (see FIG. 4). In the present exemplary embodiment, a method for acquiring a tomographic image (a plane parallel to the optical axis) of the retina 127 will be described.

Figure 5A:
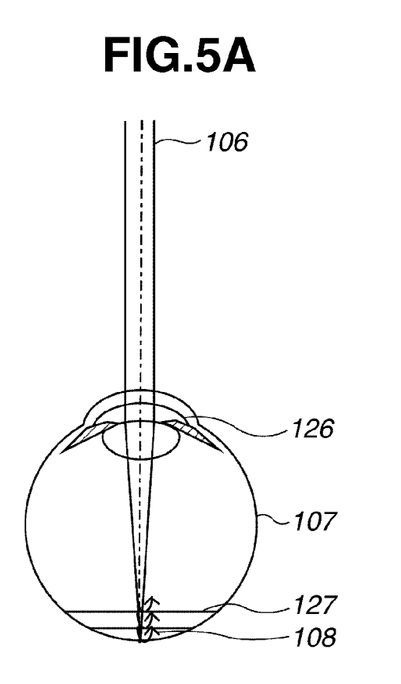
FIGS. 5A to 5C illustrate an image acquisition method in the composite apparatus according to the second exemplary embodiment of the present invention.

FIG. 5A is a schematic view of the subject's eye 107 and illustrates a state where the subject's eye 107 is observed by the composite apparatus 100. As illustrated in FIG. 5A, when the measurement beam 106 enters the retina 127 through the cornea 126, the measurement beam 106 becomes the return beams 108 due to reflection or scattering at various positions, and the return beams 108 reach the line camera 139 with delays at the respective positions.

Since the light source 101 has a large bandwidth and a short coherence length, the line camera 139 can detect an interference pattern when the optical path length of the reference optical path is approximately the same as the optical path length of the measurement optical path.

As described above, the interference pattern acquired by the line camera 139 is an interference pattern in a spectrum region on the wavelength axis.

Subsequently, the interference pattern which is information on the wavelength axis is converted into an interference pattern on an optical frequency axis by taking the characteristics of the line camera 139 and the transmission type grating 141 into consideration. Further, by performing inverse Fourier transform on the obtained interference pattern on the optical frequency axis, it is possible to obtain information in a depth direction.

Figure 5B:
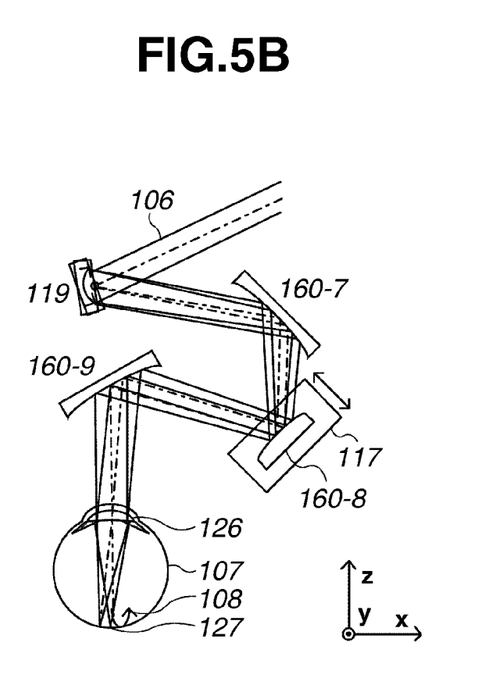
Figure 5C:
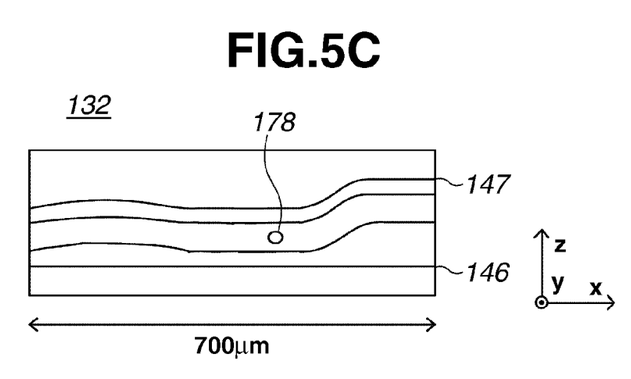

As illustrated in FIG. 5B, when the interference pattern is detected while moving the XY scanner 119, the interference pattern can be obtained at each position on the X axis. More specifically, the information in the depth direction can be obtained at each position on the X axis. As a result, a two-dimensional distribution of the intensity of the return beam 108 on the XZ plane can be obtained, which is a tomographic image 132 (see FIG. 5C).

As described above, the tomographic image 132 is one in which the intensity of the return beam 108 is arranged in an array, and the intensity is displayed by applying a gray scale. A length of the tomographic image 132 in the X direction is 700 μm, which is the same as a SLO image described below.

In the present exemplary embodiment, only the boundary of the obtained tomographic image is highlighted. The tomographic image includes a retinal pigment epithelial layer 146, a stratum opticum 147, and a blood vessel 178. When a plurality of tomographic images is acquired at each position on the Y axis, it is possible to visualize a three-dimensional movement of the blood vessel.

<SLO Image Acquisition Method>

Next, a method for acquiring a planar image (SLO image) using the composite apparatus 100 will be described. The composite apparatus 100 can acquire a planar image of the retina 127 by controlling and operating the XY scanner 119 in only the Y-axis direction and the X scanner 121 while fixing the X-axis direction of the XY scanner 119 and acquiring the intensity of the return beam 108 with the detector 138. The X scanner 121 and the XY scanner 119 are controlled by the optical scanner driver 182 in the driver unit 181 from the PC 125 (see FIG. 4).

Further, the composite apparatus 100 can acquire a planar image while correcting the aberration occurring in the subject's eye 107 by controlling the spatial light modulator 159 using the aberration of the subject's eye 107 measured by the wavefront sensor 155. Moreover, the composite apparatus 100 can acquire a planar image while controlling the spatial light modulator 159 in real time. The specific planar image acquisition method is the same as the first exemplary embodiment, and thus the description thereof will not be repeated.

<Blood Velocity Calculation Method>

A method for calculating a blood flow velocity from an acquired planar image is the same as the first exemplary embodiment, and thus the description thereof will not be repeated. The blood vessel visualized in the acquired planar image is considered to be a blood vessel which moves three-dimensionally and which is projected on the XY plane. Thus, the measured blood flow velocity is the velocity on the XY plane. As described above, the composite apparatus according to the present exemplary embodiment can grasp the three-dimensional movement of the blood vessel using a plurality of tomographic images and calculate the velocity in the XYZ space using the measured blood flow velocity on the XY plane.

As described above, the optical image capturing apparatus according to the present invention includes the splitting unit that splits a beam from the light source into a measurement beam and a reference beam, the interference unit that causes a return beam of the measurement beam irradiated on a subject's eye to interfere with the reference beam having passed through the reference optical path, and the detection unit that detects an intensity of an interference signal resulting from the interference. The optical image capturing apparatus has the function of capturing a tomographic image of the subject's eye, and most of the optical systems share the purpose of capturing tomographic images and the purpose of capturing planar images. Thus, the optical image capturing apparatus can capture planar images and tomographic images with a simple configuration and grasp a three-dimensional movement of a blood vessel. Moreover, the optical image capturing apparatus can calculate a blood flow velocity in an XYZ space.

The present invention can also be realized by executing the following processing. More specifically, software (a program) for realizing the functions of the above exemplary embodiments is supplied to a system or an apparatus via a network or various storage media and a computer (or a central processing unit (CPU) or a micro processing unit (MPU)) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-269741 filed Dec. 2, 2010, which is hereby incorporated by reference herein in its entirety.

What is claimed is:

1. An ophthalmic apparatus comprising:
   an irradiation unit configured to irradiate a subject's eye with a measurement beam scanned by a scanning unit;
   an acquisition unit configured to acquire an image of a fundus of the subject's eye based on a return beam returned from the subject's eye, of the measurement beam irradiated by the irradiation unit; and
   a calculation unit configured to calculate a blood flow velocity of the subject's eye based on a displacement between a position of a blood cell in a first image obtained by the acquisition unit and a position of the blood cell in a second image obtained by the acquisition unit at a different time from the first image and on a difference between time when the blood cell in the first image is scanned with the measurement beam by the scanning unit and time when the blood cell in the second image is scanned with the measurement beam by the scanning unit,
   wherein the difference is determined based on a time between frames and on a time for scanning the measurement beam for the displacement.

2. The ophthalmic apparatus according to claim 1, wherein the calculation unit calculates the time when the blood cell in the image is scanned with the measurement beam by the scanning unit based on the position of the blood cell in the image acquired by the acquisition unit.

3. The ophthalmic apparatus according to claim 1, further comprising a display unit configured to display the image of the subject's eye acquired by the acquisition unit.

4. The ophthalmic apparatus according to claim 3, further comprising an image processing unit configured to perform image processing on the first image and the second image so that the blood cell included in the first and second images is highlighted and displayed on the display unit.

5. The ophthalmic apparatus according to claim 3, further comprising a selection unit configured to select the blood cell included in the first image and the second image displayed on the display unit,
- wherein the calculation unit calculates the blood flow velocity of the subject's eye based on the displacement and the difference of the blood cell included in the first image and the second image, selected by the selection unit.

6. The ophthalmic apparatus according to claim 1, further comprising an image creation unit configured to create a spatiotemporal image using the first image and the second image.

7. The ophthalmic apparatus according to claim 1, further comprising:
- an aberration measurement unit configured to measure an aberration occurring in the subject's eye;
- a spatial light modulation unit which is disposed at a position conjugate to the aberration measurement unit and configured to modulate at least one of the measurement beam and the return beam; and
- a control unit configured to control an amount of modulation in the spatial light modulation unit based on a measurement result by the aberration measurement unit to correct the aberration.

8. The ophthalmic apparatus according to claim 1, further comprising:
- a splitting unit configured to split a beam from a light source into the measurement beam and a reference beam;
- an interference unit configured to cause the return beam from the measurement beam irradiated to the subject's eye to interfere with the reference beam having passed through a reference optical path;
- a detection unit configured to detect intensity of an interference signal resulting from the interference; and
- a tomographic image acquisition unit configured to acquire a tomographic image of the subject's eye based on the intensity detected by the detection unit.

9. The ophthalmic apparatus according to claim 8, further comprising:
- a conversion unit configured to detect the return beam, from the subject's eye, of the measurement beam and converts the detected beam into an electrical signal; and
- a light guiding unit configured to guide the return beam to the conversion unit on an optical path that connects the light source and the subject's eye,
- wherein the acquisition unit acquires the image of the subject's eye based on intensity of the electrical signal obtained by the conversion unit.

10. A method for calculating a blood flow velocity, the method comprising:
- irradiating a subject's eye with a measurement beam scanned by a scanning unit;
- acquiring an image of a fundus of the subject's eye based on a return beam, from the subject's eye, of the irradiated measurement beam; and
- calculating a blood flow velocity of the subject's eye based on a displacement between a position of a blood cell in an acquired first image and a position of the blood cell in a second image acquired at a different time from the first image and a difference between time when the blood cell in the first image is scanned with the measurement beam by the scanning unit and time when the blood cell in the second image is scanned with the measurement beam by the scanning unit,
- wherein the difference is determined based on a time between frames and on a time for scanning the measurement beam for the displacement.

11. A non-transitory computer readable medium having program code stored thereon to perform a method for calculating a blood flow velocity, the method comprising:
- irradiating a subject's eye with a measurement beam scanned by a scanning unit;
- acquiring an image of a fundus of the subject's eye based on a return beam, from the subject's eye, of the irradiated measurement beam; and
- calculating a blood flow velocity of the subject's eye based on a displacement between a position of a blood cell in an acquired first image and a position of the blood cell in a second image acquired at a different time from the first image and a difference between time when the blood cell in the first image is scanned with the measurement beam by the scanning unit and time when the blood cell in the second image is scanned with the measurement beam by the scanning unit,
- wherein the difference is determined based on a time between frames and on a time for scanning the measurement beam for the displacement.

* * * * *